(12) United States Patent
Wubbels et al.

(10) Patent No.: US 12,201,357 B1
(45) Date of Patent: Jan. 21, 2025

(54) DIAGNOSTIC MODEL OPTIMIZATION FOR VARIATIONS IN MECHANICAL COMPONENTS OF IMAGING DEVICES

(71) Applicant: Verily Life Sciences LLC, Mountain View, CA (US)

(72) Inventors: Peter Wubbels, Redwood City, CA (US); Lin Yang, Sunnyvale, CA (US); Eliezer Glik, San Francisco, CA (US); Sam Kavusi, Menlo Park, CA (US)

(73) Assignee: Verily Life Sciences LLC, Dallas, TX (US)

( * ) Notice: Subject to any disclaimer, the term of this patent is extended or adjusted under 35 U.S.C. 154(b) by 189 days.

(21) Appl. No.: 17/805,833

(22) Filed: Jun. 7, 2022

Related U.S. Application Data

(63) Continuation of application No. 16/752,548, filed on Jan. 24, 2020, now Pat. No. 11,357,396.
(Continued)

(51) Int. Cl.
*A61B 3/00* (2006.01)
*G06T 7/00* (2017.01)
*G06V 20/69* (2022.01)

(52) U.S. Cl.
CPC .......... *A61B 3/0025* (2013.01); *G06T 7/0012* (2013.01); *G06V 20/69* (2022.01);
(Continued)

(58) Field of Classification Search
CPC ......... G06T 7/0012; G06T 2207/20081; G06T 2207/30041; G06V 20/69; A61B 3/0025; A61B 2576/02
See application file for complete search history.

(56) References Cited

U.S. PATENT DOCUMENTS

| 10,235,601 B1 | 3/2019 | Wrenninge et al. |
| 2017/0169620 A1* | 6/2017 | Bleiweiss ............ G06V 20/64 |

(Continued)

FOREIGN PATENT DOCUMENTS

| CN | 107492090 A | 12/2017 |
| WO | 2018008593 A1 | 1/2018 |

OTHER PUBLICATIONS

Gao et al. "Diagnosis of Diabetic Retinopathy Using Deep Neural Networks." IEEE Access, Dec. 19, 2018, pp. 3360-3370 ( Year: 2018).
(Continued)

*Primary Examiner* — Jon Chang
(74) *Attorney, Agent, or Firm* — Perkins Coie LLP

(57) ABSTRACT

Introduced here are diagnostic platforms able to optimize computer-aided diagnostic (CADx) models by simulating the optical performance of an imaging device based on its mechanical components. For example, a diagnostic platform may acquire a source image associated with a confirmed diagnosis of a medical condition, simulate optical performance based on design data corresponding to a virtual prototype of the imaging device, generate a training image by altering the source image based on the optical performance, apply a diagnostic model to the training image, and then determine whether the performance of the diagnostic model meets a specified performance threshold. If the diagnostic model fails to meet the specified performance threshold, the diagnostic platform can automatically optimize the diagnostic model for the imaging device by altering its underlying algorithm(s).

25 Claims, 9 Drawing Sheets

Related U.S. Application Data

(60) Provisional application No. 62/797,104, filed on Jan. 25, 2019.

(52) U.S. Cl.
CPC . *A61B 2576/02* (2013.01); *G06T 2207/20081* (2013.01); *G06T 2207/30041* (2013.01)

(56) References Cited

U.S. PATENT DOCUMENTS

| | | |
|---|---|---|
| 2019/0221313 A1 | 7/2019 | Rim et al. |
| 2020/0069175 A1 | 3/2020 | Kumagai et al. |
| 2020/0372632 A1 | 11/2020 | Chauhan |

OTHER PUBLICATIONS

Yang et al. "Crossing-Domain Generative Adversarial Networks for Unsupervised Multi-Domain Image-to-Image Translation." Proceedings of the 26th ACM International Conference on Multimedia, Oct. 15, 2018, pp. 374-382 (Year: 2018).

* cited by examiner

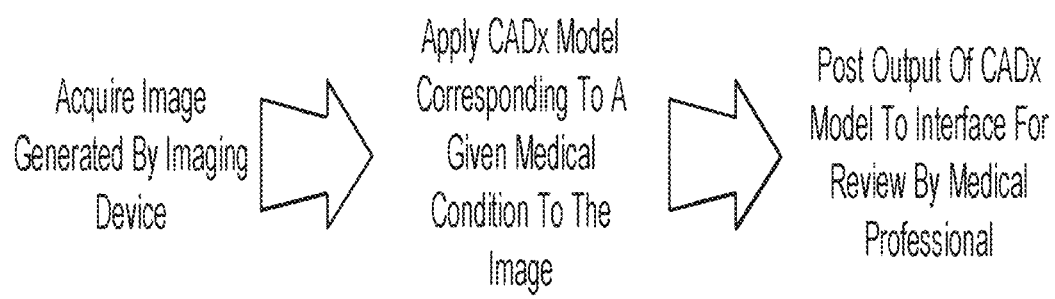
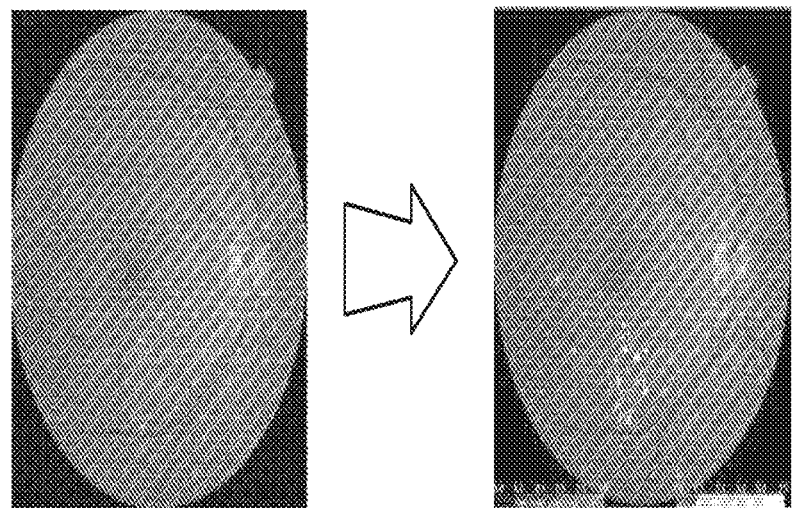
FIGURE 1

200

201
Identify cohort of individuals that have a specified distribution of medical conditions

202
Acquire images of the cohort of individuals generated by a camera to be validated

203
Apply CADx model to the acquired images

Does performance exceed specified threshold?

Yes → 204 Certify the CADx model has been validated for the camera

No → 205 Acquire more training data for the camera

801
Acquire a first set of images generated by a first imaging device

802
Identify a second imaging device for which a diagnostic model is to be optimized

803
Acquire a second set of images generated by the second imaging device

804
Apply a translation algorithm to discover how to translate a first image in the first set of images into a corresponding second image in the second set of images

805
Optimize a diagnostic model for the second imaging device based on the translation scheme

806
Save the optimized diagnostic model in a database

807
Associate the optimized diagnostic model with the second imaging device

FIGURE 8

DIAGNOSTIC MODEL OPTIMIZATION FOR VARIATIONS IN MECHANICAL COMPONENTS OF IMAGING DEVICES

CROSS-REFERENCE TO RELATED APPLICATIONS

This application is a continuation of U.S. application Ser. No. 16/752,548, filed Jan. 24, 2020, which claims priority to U.S. Provisional Application No. 62/797,104, titled "Diagnostic Model Optimization for Variations in Mechanical Components of Imaging Devices" and filed on Jan. 25, 2019, each of which is incorporated by reference herein in its entirety.

TECHNICAL FIELD

Various embodiments concern computer programs and associated computer-implemented techniques for optimizing a diagnosis model to account for variations in the mechanical components of an imaging device.

BACKGROUND

Computer-aided detection and diagnosis technologies can be used to assist medical professionals in interpreting images to render diagnoses. Imaging technologies such as x-ray, magnetic resonance imaging (MRI), and ultrasound yield a substantial amount of information that a medical professional must evaluate in a short time. To expedite this process, a computer-implemented platform (or simply "platform") may process digital images and highlight conspicuous sections to offer input in support of a decision rendered by the medical professional.

Computer-aided detection technologies are usually confined to marking conspicuous structures, sections, etc., discovered in a digital image. Computer-aided diagnosis technologies, meanwhile, may take the additional step of automatically evaluating these conspicuous structures, sections, etc. For example, in mammography, a platform may highlight microcalcification clusters in the soft tissue that may be largely indistinguishable to the human eye. Such action may permit a medical professional to draw conclusions about the condition of the pathology, the progress of the pathology, etc.

While the platform may be implemented in a clinical environment, the platform will normally support, rather than replace, the medical professional. Accordingly, the medical professional is generally responsible for the final interpretation of any outputs produced by computer-aided diagnosis technologies. As noted above, however, some platforms may be able to detect early signs of abnormalities that humans cannot, so a platform may play a key role in rendering diagnoses.

And yet there are invariably variations in the mechanical components in imaging and other sensory devices coupled to these platforms. These variations can adversely impact a platform's ability to accurately render diagnoses. As such, technologies that can reduce the adverse impact of these variations are desirable.

BRIEF DESCRIPTION OF THE DRAWINGS

Various features of the technology will become more apparent to those skilled in the art from a study of the Detailed Description in conjunction with the drawings. Embodiments of the technology are illustrated by way of example and not limitation in the drawings, in which like references may indicate similar elements.

FIG. 1 illustrates an example scenario in which a diagnostic platform acquires a retinal image generated by a fundus camera, applies a computer-aided diagnostic (CADx) model corresponding to a given ailment to the retinal image, and then posts an output produced by the CADx model to an interface for review by a medical professional.

FIG. 2 depicts a flow diagram of an example process for validating a CADx model for a new imaging device.

FIG. 8 depicts a flow diagram of a process for validating a diagnostic model associated with a medical condition for a proposed imaging device based on image translation.

Figure 3:
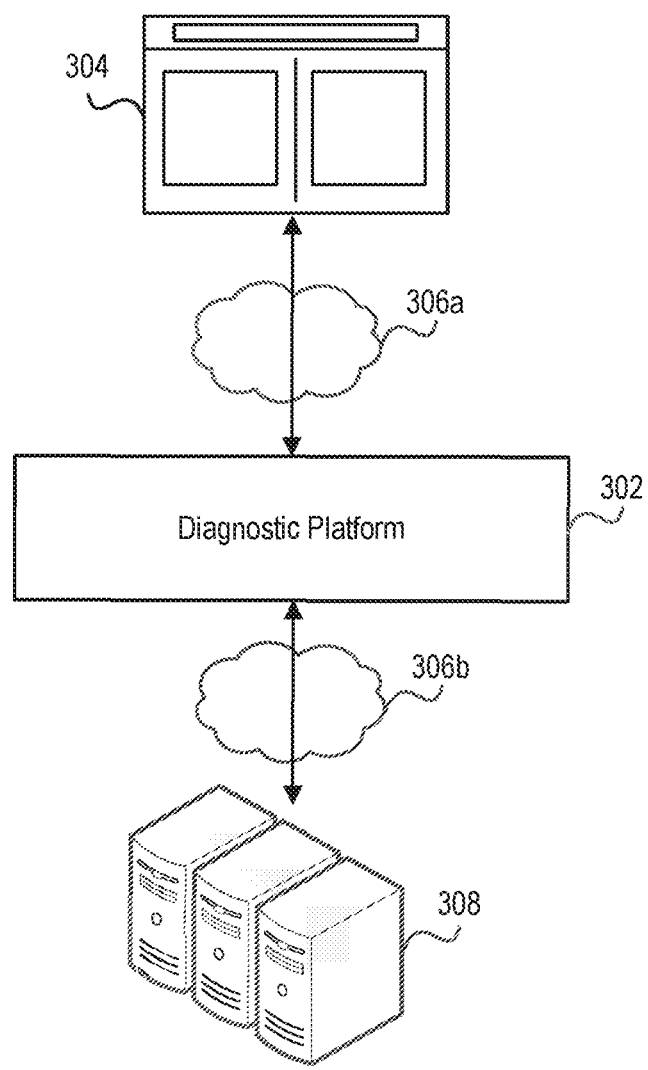
FIG. 3 illustrates a network environment that includes a diagnostic platform.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Imaging has historically been the most effective means for detecting a variety of ailments. For example, radiological imaging (which can include computed tomography (CT), fluoroscopy, mammography, ultrasound, and MRI) has been shown to be the most effective means for early detection of breast cancer, while fundus photography has been shown to be the most effective means for early detection of diabetic retinopathy (DR). However, differentiating the features in an image can be difficult. For instance, the differences between benign and malignant growths may be largely indistinguishable to the human eye.

Accordingly, computer-aided diagnosis technologies have become a part of routine clinical work in several areas of medicine. To increase the accuracy of image interpretation, a diagnostic platform can apply one or more computer-aided diagnostic (CADx) models to an image. FIG. 1 illustrates an example scenario in which a diagnostic platform acquires a retinal image generated by a fundus camera, applies a CADx model corresponding to a given ailment to the retinal image, and then posts an output produced by the CADx model to an interface for review by a medical professional. In some instances the output is a proposed diagnosis with respect to the given ailment, while in other instances the output is intended to facilitate the rendering of a diagnosis. For example, the output may include an image in which the feature(s) determined to be diagnostically relevant by the diagnostic platform have been visually highlighted in some manner.

In general, each CADx model is designed to apply algorithm(s) to an image to produce an output that conveys information about a corresponding ailment or disease (collectively referred to as "medical conditions"). The output is normally considered as a "second opinion" by the medical professional responsible for interpreting the image. Thus, CADx models can act as decision aids for medical professionals (e.g., radiologists and ophthalmologists) in characterizing the features of an image.

The algorithm(s) of a CADx model will generally perform several different processes via the use of tools such as artificial neural networks (ANN). These processes can include image processing, feature analysis, and data classification. However, the output produced by these algorithm(s) may depend on the characteristics of the images provided as input. For example, a given CADx model may produce different outputs (e.g., different proposed diagnoses) if multiple versions of the same image having different contrast levels are provided as input. Consequently, a CADx model must be "tuned" or "trained" prior to deployment of the imaging device responsible for generating the images that will be examined by the CADx model.

One way to validate a CADx model prior to deployment for a given imaging device is to use a set of validation images and accompanying truth labels, which represent verified diagnoses provided by human graders (e.g., medical professionals, such as radiologists and ophthalmologists). FIG. 2 depicts a flow diagram of an example process for validating a CADx model for a new imaging device. Initially, an entity identifies a cohort of individuals that have a specified distribution of medical conditions (step 201). For example, the entity may identify 1,000 individuals with a specified distribution of diabetic retinopathy (DR) conditions (e.g., 200 healthy, 200 DR mild, 200 DR moderate, 200 DR severe, 200 DR proliferate). These diagnoses may be referred to as "truth labels." Generally, the entity is responsible for developing, updating, and managing CADx models for various medical conditions.

Thereafter, the entity can acquire images of the cohort of individuals generated by a target camera to be validated (step 202). A CADx model is then applied to the acquired images (step 203), and the outputs produced by the CADx model are compared with the truth labels. If the performance of the CADx model meets a specified performance metric (e.g., an F1 score of greater than 0.9), then the entity can certify that the diagnostic model has been validated for the target camera (step 204). However, if the performance of the CADx model fails to meet the specified performance metric, then more training data (e.g., in the form of more retinal images) is captured by the target camera (step 205) and the CADx model is tuned using the new training data. These steps can be repeated until the performance of the CADx model meets the specified performance metric.

However, such a process suffers from several downsides. For instance, the images produced by a new imaging device may be subjected to multiple CADx models corresponding to different medical conditions. But because the entire validation process must be performed for each CADx model, deployment of the new imaging device can result in significant operational hassle. Moreover, the options for improving robustness of these CADx models are often extremely limited. For example, to improve robustness of a CADx model, the entity may add augmented images that have been subjected to simple image operations to the training data used to optimize the CADx model. Examples of simple image operations include rotating, mirroring, or altering an image property (e.g., hue or saturation). However, the augmentations produced by these simple image operations are entirely unrelated to the imaging devices used to generate the images. Consequently, the augmentations serve little purpose in strengthening CADx models.

Introduced here, therefore, are diagnostic platforms able to optimize CADx models (also referred to as "diagnostic models") by simulating the electromagnetic transformation function of an imaging device. Thus, a diagnostic platform may simulate the optical performance of the imaging device by predicting how light will be transmitted, reflected, or transformed by the mechanical components of an imaging device. For example, a diagnostic platform may acquire a series of images and corresponding truth labels, augment the series of images to mimic the effect of a variation in the mechanical components of an imaging device, and then apply a diagnostic model to the series of augmented images to produce a series of outputs. By comparing the series of outputs and the corresponding truth labels, the diagnostic platform can automatically optimize the diagnostic model for the imaging device prior to deployment. These augmentations may correspond to changes to, or the introduction of, blurriness, resolution, contrast, white balance, shading, scattering, distortion, color aberrations, sharpening, compression, or any combination thereof. The variation, meanwhile, may be the addition of a new hardware component, the alteration of a characteristic of an existing hardware component (e.g., to simulate a defect), etc. As further described below, the effect of the variation may be estimated by a specialized computer program designed to simulate how light rays will travel through the imaging device.

Embodiments may be described with reference to particular medical conditions, computer programs, system configurations, networks, etc. However, those skilled in the art will recognize that these features are equally applicable to other medical conditions, computer program types, system configurations, network types, etc. For example, although embodiments may be described in the context of diagnostic models to be applied to retinal images generated by retinal cameras generated by fundus cameras (also referred to as "retinal cameras"), the relevant features may be equally applicable to diagnostic models to be applied to images of other parts of the human body.

Moreover, the technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program a computing device to perform a process for acquiring source images associated with confirmed diagnoses of a medical condition, simulating optical performance of an imaging device based on design data corresponding to a virtual prototype of the imaging device, generating training images by altering the source images based on the optical performance, applying a diagnostic model to the training images, determining whether the performance of the diagnostic model meets a specified performance metric, altering the diagnostic model to ensure that future applications to images generated by the imaging device will meet the specified performance metric, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Technology Overview

FIG. 3 illustrates a network environment 300 that includes a diagnostic platform 302. Individuals can interface with the diagnostic platform 302 via an interface 304. For example, administrators may access the interface 304 to develop/train diagnostic models, while medical professionals may access the interface 304 to review outputs produced by diagnostic models. The diagnostic platform 302 may be responsible for developing diagnostic models to be applied to images taken of subjects (also referred to as "patients"), applying the diagnostic models to images to identify the clinically- or diagnostically-relevant segment(s), generating records of the outputs produced by the diagnostic models, etc.

When applied to an image received from an imaging device, the diagnostic model may produce an output indicative of the health state of a corresponding subject. Examples of imaging devices include retinal cameras, x-ray generators and detectors, MRI machines, CT machines, digital cameras (e.g., digital single-lens reflex (DSLR) cameras and mirrorless cameras), etc. Some diagnostic models produce proposed diagnoses that can be examined by a medical professional, while other diagnostic models produce a visualization component intended to help the medical professional render a diagnosis. For example, the application of a diagnostic model to the image may cause the segment(s) determined to be diagnostically relevant to be highlighted, outlined, etc. The term "health state" can refer to the physical health of the subject with respect to a given medical condition. For example, some diagnostic platforms are designed to identify/monitor digital features known to be indicative of diabetic retinopathy (DR), while other diagnostic platforms are designed to identify/monitor features in images known to be indicative of breast cancer. The diagnostic platform 302 may also be responsible for creating interfaces through which individuals can view subject information (e.g., name, weight, medical history), review estimations of the health state, manage preferences, etc.

As shown in FIG. 3, the diagnostic platform 302 may reside in a network environment 300. Thus, the diagnostic platform 302 may be connected to one or more networks 306a-b. The network(s) 306a-b can include personal area networks (PANs), local area networks (LANs), wide area networks (WANs), metropolitan area networks (MANs), cellular networks, the Internet, etc. Additionally or alternatively, the diagnostic platform 302 can be communicatively coupled to computing device(s) over a short-range communication protocol, such as Bluetooth® or Near Field Communication (NFC).

The interface 304 is preferably accessible via a web browser, desktop application, mobile application, or over-the-top (OTT) application. Accordingly, the interface 304 may be viewed on a personal computer, tablet computer, mobile workstation, personal digital assistant (PDA), mobile phone, game console, music player, wearable electronic device (e.g., a watch or fitness accessory), network-connected ("smart") electronic device, (e.g., a television or home assistant device), virtual/augmented reality system (e.g., a head-mounted display), or some other electronic device.

Some embodiments of the diagnostic platform 302 are hosted locally. That is, the diagnostic platform 302 may reside on the computing device used to access the interface 304. For example, the diagnostic platform 302 may be embodied as a mobile application executing on a mobile phone or a desktop application executing on a mobile workstation. Other embodiments of the diagnostic platform 302 are executed by a cloud computing service operated by Amazon Web Services® (AWS), Google Cloud Platform™, Microsoft Azure®, or a similar technology. In such embodiments, the diagnostic platform 302 may reside on a host computer server that is communicatively coupled to one or more content computer servers 308. The content computer server(s) 308 can include images to be examined for the purpose of rendering diagnoses, subject information (e.g., age, sex, health diagnoses, etc.), imaging device information (e.g., resolution, expected file size, etc.), diagnostic models, and other assets. Such information could also be stored on the host computer server.

Certain embodiments are described in the context of network-accessible interfaces. However, those skilled in the art will recognize that the interfaces need not necessarily be accessible via a network. For example, a computing device may be configured to execute a self-contained computer program that does not require network access. Instead, the self-contained computer program may cause necessary assets (e.g., images, diagnostic models, or processing operations) to be downloaded at a single point in time or on a periodic basis (e.g., weekly, daily, or hourly).

Figure 4:
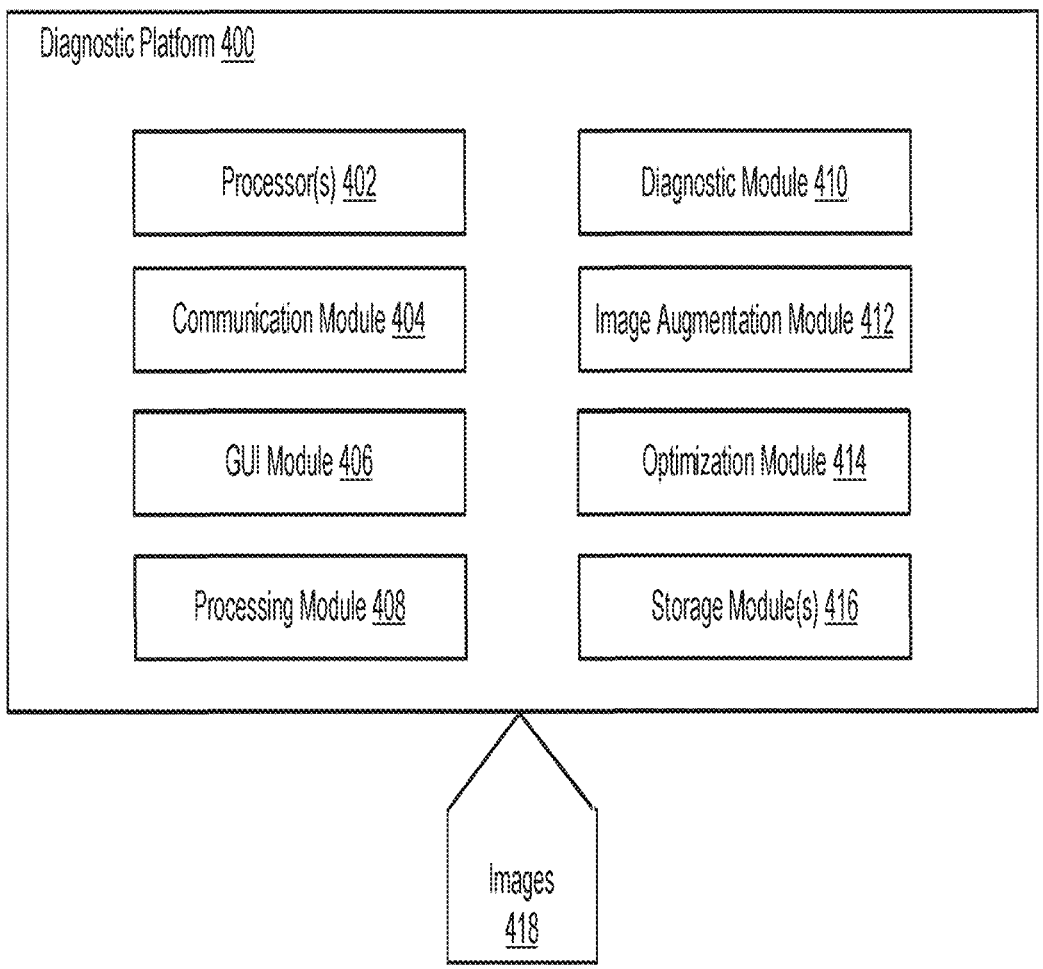
FIG. 4 depicts the high-level architecture of a diagnostic platform able to optimize diagnostic models for newly-developed imaging devices by simulating the optical performance of these imaging devices.

FIG. 4 depicts the high-level architecture of a diagnostic platform 400 able to optimize diagnostic models for newly-developed imaging devices by simulating the optical performance of these imaging devices. The diagnostic platform 400 may simulate the optical performance of an imaging device based on design data corresponding to a virtual prototype of the imaging device. Such action enables the diagnostic platform 400 to predict the impact of the hardware components of the imaging device on optical performance (as well as optimize diagnostic models to be applied to images produced by the imaging device) prior to manufacture and/or deployment of the imaging device. As shown in FIG. 3, an individual can interface with the diagnostic platform 400 via an interface. The individual may be an administrator responsible for developing/training diagnostic models or a medical professional responsible for reviewing the outputs produced by diagnostic models.

The diagnostic platform 400 can include one or more processors 402, a communication module 404, a graphical user interface (GUI) module 406, a processing module 408, a diagnostic module 410, an image augmentation module 412, an optimization module 414, and one or more storage modules 416. In some embodiments a single storage module includes multiple computer programs for performing different operations (e.g., metadata extraction, image processing, digital feature analysis), while in other embodiments each computer program is hosted within a separate storage module. Embodiments of the diagnostic platform 400 may include some or all of these components, as well as other components not shown here.

The processor(s) 402 can execute modules from instructions stored in the storage module(s) 416, which can be any device or mechanism capable of storing information. For example, the processor(s) 402 may execute the GUI module 406, processing module 408, diagnostic module 410, image augmentation module 412, or optimization module 414.

The communication module 404 can manage communications between various components of the diagnostic platform 400. The communication module 404 can also manage communications between the computing device on which the diagnostic platform 400 resides and another computing device.

For example, the diagnostic platform 200 may reside on a mobile workstation in the form of a desktop application. In such embodiments, the communication module 404 can facilitate communication with a network-accessible computer server responsible for supporting the desktop application and/or an imaging device responsible for generating images of subjects. The communication module 404 may facilitate communication with various data sources through the use of application programming interfaces (APIs), bulk data interfaces, etc. Examples of data sources include network-accessible databases, other desktop applications residing on the mobile workstation, etc.

As another example, the diagnostic platform 400 may reside on a server system that includes one or more network-accessible computer servers. In such embodiments, the communication module 404 can communicate with a computer program executing on a computing device accessible to an individual, such as a mobile phone, desktop computer, or mobile workstation. For example, an administrator may optimize a diagnostic model for a given imaging device by interacting with the diagnostic platform 400 via a web browser. As another example, a medical professional may review outputs produced by a diagnostic model by interacting with the diagnostic platform 400 via a web browser. Those skilled in the art will recognize that the components of the diagnostic platform 400 can be distributed between the server system and the computing device in various manners. For example, some data (e.g., images of subjects) may reside on the computing device for privacy purposes, while other data (e.g., processing operations for detecting digital features in images, rendering proposed diagnoses based on the digital features, and estimating the health state of subjects) may reside on the server system.

The GUI module 406 can generate the interface(s) through which an individual can interact with the diagnostic platform 400. For example, an interface may include an image of a body part that includes one or more digital features (e.g., highlighted segments or outlined segments) intended to assist in rendering a diagnosis with respect to a given medical condition. As another example, an interface may include information regarding a diagnostic model designed to assist medical professionals by visually distinguishing the diagnostically-important segments of an image. One example of such information is a proposed diagnosis. As another example, an interface may include optical design data related to a virtual prototype of an imaging device in a computer-aided design (CAD) environment.

The processing module 408 can apply one or more operations to images 418 acquired by the diagnostic platform 400. For example, the processing module 408 may extract metadata to discover characteristic(s) of the subject included in each image or the imaging device responsible for generating each image. As another example, the processing module 408 may alter the pixel data of each image in some manner (e.g., by altering contrast, brightness, etc.). As further described below, the images 418 could be acquired from one or more sources. Examples of sources include the computing device on which the diagnostic platform 400 resides and an imaging device to which the computing device is connected. In some embodiments, different types of images are acquired by the diagnostic platform 400 from multiple sources (e.g., different imaging devices). For example, the diagnostic platform 400 could acquire two-dimensional (2D) images, three-dimensional (3D) images, colored images, grayscale images (e.g., those captured during a fluorescein angiography procedure), etc. Thus, the processing module 408 may apply operation(s) to ensure that images 418 received from multiple sources are in a compatible format that can be processed by the other modules.

A source may be configured to continuously or periodically transmit images 418 to the diagnostic platform 400. In some embodiments, the source continually uploads images 218 to the health management platform 400 so long as the source remains communicatively coupled to the computing device on which the diagnostic platform 400 resides (e.g., via a Bluetooth® communication channel). For example, images 418 may be streamed from the source to the diagnostic platform 400 in real time as the images 418 are generated. In other embodiments, the source uploads images 418 to the diagnostic platform 400 on a periodic basis (e.g., hourly, daily, or weekly). The diagnostic platform 400 can be configured to pull images 418 from the source. Additionally or alternatively, the source can be configured to push images 418 to the diagnostic platform 400. In some embodiments, an individual (e.g., an administrator or a medical professional) is able to configure these push/pull settings. These settings can be configured on a source-by-source basis.

Upon receiving an image, the diagnostic module 410 can identify an appropriate diagnostic model to apply to the image. Generally, the diagnostic model is one of multiple diagnostic models maintained in a library stored in the storage module(s) 416, and each diagnostic model may be associated with a different medical condition. The diagnostic model can include algorithm(s) that, when applied to the pixel data of the image, produce an output that conveys information about a medical condition. For example, if the image is a retinal image generated by a retinal camera, the output of the diagnostic model may provide information regarding an eye-related medical condition such as diabetes, age-macular degeneration (AMD), glaucoma, neoplasm, DR, etc. The output is normally considered as a "second opinion" by the medical professional responsible for interpreting the image. However, in some embodiments, the output may be representative of a direct diagnostic decision (e.g., no medical professional may be involved).

Because the output produced by a diagnostic model depends on the pixel data of the image provided as input, the diagnostic model must be "tuned" or "trained" for each imaging device that can act as a source. Conventionally, a diagnostic model is validated for a given imaging device using a set of validation images and accompanying truth labels, which represent verified diagnoses provided by human graders (e.g., medical professionals, such as radiologists and ophthalmologists). However, this process can quickly become onerous as multiple diagnostic models could be applied to a single image. The image augmentation module 412 can address this issue by simulating the optical performance of a proposed imaging device based on design data corresponding to a virtual prototype of the proposed imaging device. Initially, the image augmentation module 412 can acquire a source image and accompanying truth label, which represents a verified diagnosis of a medical condition that was provided by a human grader. Then, the image augmentation module 412 can simulate the optical performance of the proposed imaging device. Based on the simulated optical performance, the image augmentation module 412 can augment the source image to produce a training image intended to mimic the source image as if generated by the proposed imaging device. For example, the image augmentation module 412 may augment the source image by changing/introducing blurriness, resolution, contrast, white balance, shading, scattering, distortion, color aberrations, sharpening, compression, or any combination thereof.

In some embodiments, the image augmentation module 412 is configured to simulate the optical performance of the proposed imaging device by simulating how light rays will travel through its mechanical components. Such action may be performed despite the proposed imaging device being in the prototype stage. Accordingly, the image augmentation module 412 may access design data related to a virtual prototype of the proposed imaging device in a computer-aided design (CAD) environment, and then simulate optical performance using the design data. The image augmentation module 412 may be able to parse the design data to identify characteristic(s) of the mechanical components of the imaging device. For example, the image augmentation module 412 may be able to identify the types, strengths, power stabilities, wavelength variations (e.g., due to the light source), spherical aberrations, coma aberrations, chromatic aberrations, astigmatisms, field curvatures, distortions (e.g., due to lens imperfections/defects), sensitivities, signal-to-noise (SNR) ratios, dark noises (e.g., due to variations in imaging sensors), etc., of mechanical component(s) arranged in the optical path along which light rays will travel during the imaging process. Examples of mechanical components include lenses, mirrors, light sources, and imaging sensors such as charge-coupled devices (CCDs), complementary metal-oxide-semiconductors (CMOSs), and photomultiplier tubes (PMTs). Additionally or alternatively, the image augmentation module 412 may simulate process variations by altering the position of a given mechanical component from its designated/preferred position. For example, the image augmentation module 412 may examine the design data to identify the coordinates of a lens and then alter the position of the lens (e.g., by shifting the lens 0.5 millimeter (mm), 1 mm, etc.) by a specified amount. Process variations are generally representative of defects that may be introduced during the manufacturing process.

In other embodiments, the image augmentation module 412 may be communicatively connected to a computer program (e.g., via the communication module 404) that is designed to simulate the performance of a proposed imaging device by simulating how light rays will travel through its mechanical components. In such embodiments, the image augmentation module 412 may receive results of the simulation from the computer program, and then use the results to identify an appropriate augmentation to introduce to the source image.

Those skilled in the art will recognize that the image augmentation module 412 could produce any number of training images based on variations on the design of the proposed imaging device. For instance, responsive to determining that the design data has been altered due to a change to the virtual prototype of the proposed imaging device, the image augmentation module 412 may produce a new training image. The change may correspond to a change in a mechanical component of the proposed imaging device, a change in a property of the mechanical component (e.g., to simulate a defect), etc.

Thereafter, the optimization module 414 can apply a diagnostic model to the training image to produce an output and then determine whether the output meets a specified performance metric. For example, if the image augmentation module 412 produced a single training image, the optimization module 414 may determine whether the output is substantially identical to the truth label that accompanied the source image. As another example, if the image augmentation module 412 produced a series of training images based on different source images, the optimization module 414 may determine whether the application of the diagnostic model to the series of training images results in an F1 score (also referred to as an "F Score" or "F Measure") of greater than 0.85, 0.9, 0.95, etc.

Such action allows the optimization module 414 to determine whether the diagnostic model needs to be tailored for the proposed imaging device. If the optimization module 414 discovers that the output does not meet the specified performance metric, the optimization module 414 may alter the diagnostic model to ensure that future applications of the diagnostic model will meet the specified performance metric. For example, the image augmentation module 412 may be applied to all of the training images from all imaging devices to simulate how these images would look if captured by the proposed imaging device. Then, the optimization module 414 may use these augmented training images and the truth labels that accompanied the original training images to train a new diagnostic model that is more informed about the optical attribution of the proposed imaging device. Thus, the optimization module 414 may produce different versions of a diagnostic model for different imaging devices. In another setting, the optimization module 414 may use the augmented training images and original training images to train a diagnostic model that can meet certain performance requirement(s) on an existing imaging device and/or a proposed imaging device.

Figure 5:
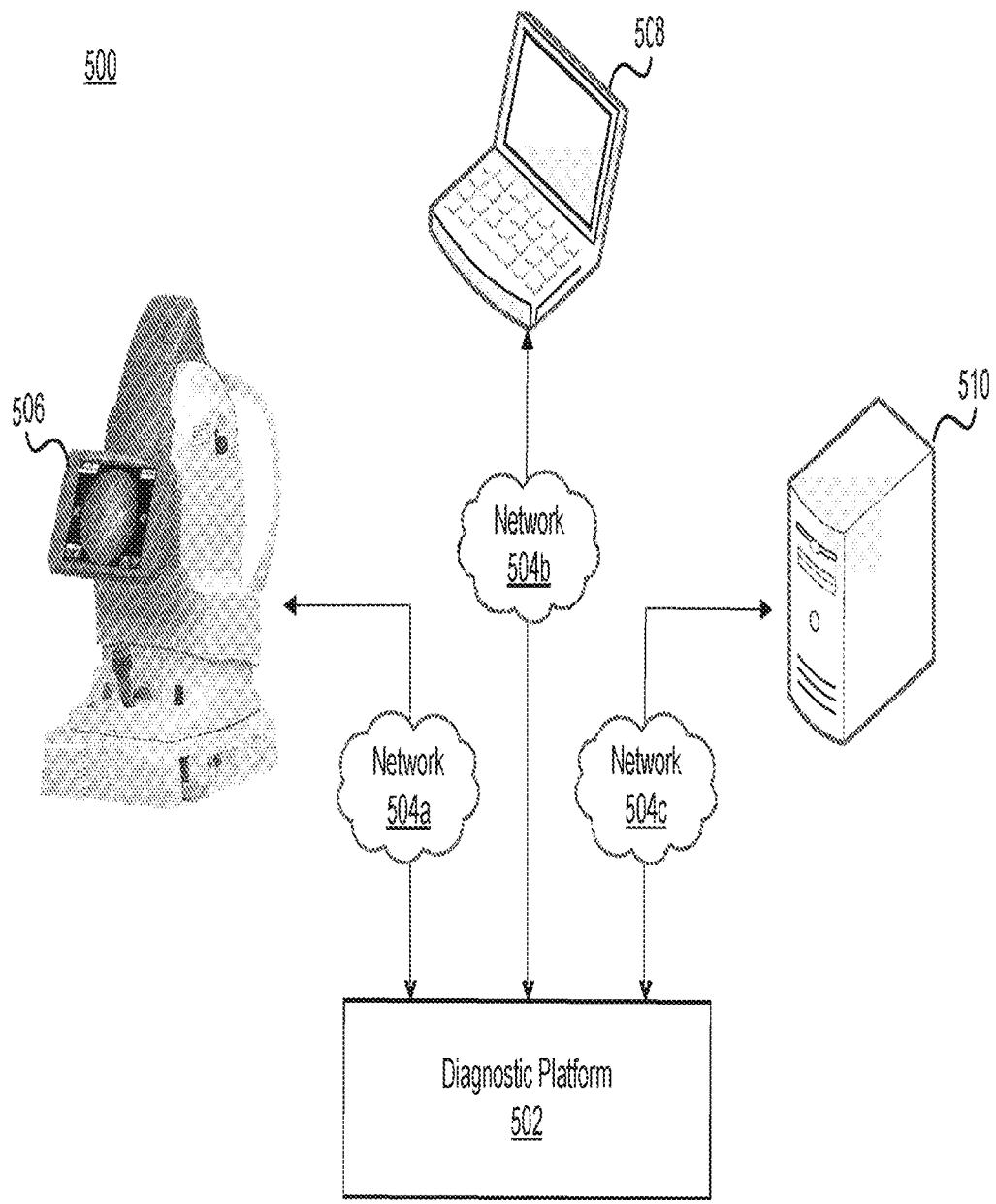
FIG. 5 depicts an example of a communication environment that includes a diagnostic platform configured to acquire images acquired from one or more sources.

FIG. 5 depicts an example of a communication environment 500 that includes a diagnostic platform 502 configured to acquire images acquired from one or more sources. Here, for example, the diagnostic platform 502 receives images from a retinal camera 506, laptop computer 508, and network-accessible server system 510 (collectively referred to as the "networked devices").

The networked devices can be connected to the diagnostic platform 502 via one or more computer networks 504a-c. The computer network(s) 504a-c can include PANs, LANs, WANS, MANs, cellular networks, the Internet, etc. Additionally or alternatively, the networked devices may communicate with one another over a short-range communication protocol, such as Bluetooth® or Near Field Communication (NFC). For example, the diagnostic platform 502 resides on the network-accessible server system 510 in some embodiments. In such embodiments, data received from the network-accessible server system 510 need not traverse any computer networks. However, the network-accessible server system 510 may be connected to the retinal camera 506 and the laptop computer 508 via separate Wi-Fi communication channels.

Embodiments of the communication environment 500 may include some or all of the networked devices. For example, some embodiments of the communication environment 500 include a diagnostic platform 502 that receives images from the retinal camera 506 and the network-accessible server system 510 on which it resides. As another example, some embodiments of the communication environment 500 include a diagnostic platform 502 that receives images from a variety of different retinal cameras located in different environments (e.g., different clinics).

The diagnostic platform 502 can acquire images in at least two different scenarios. First, the diagnostic platform 502 may acquire images to be used in the training of a diagnostic model for a given imaging device. Because these images are accompanied by truth labels that have been verified by human graders, these images are generally acquired from the network-accessible server system 510. Second, the diagnostic platform 502 may acquire images to which diagnostic model(s) are to be applied. Generally, these images are received directly from an imaging device (e.g., the retinal camera 506), though in some instances these images may be transmitted from the imaging device to the diagnostic platform 502 via an intermediary object (e.g., a storage mechanism managed by a hospital, clinic, research entity, etc.).

Figure 6:
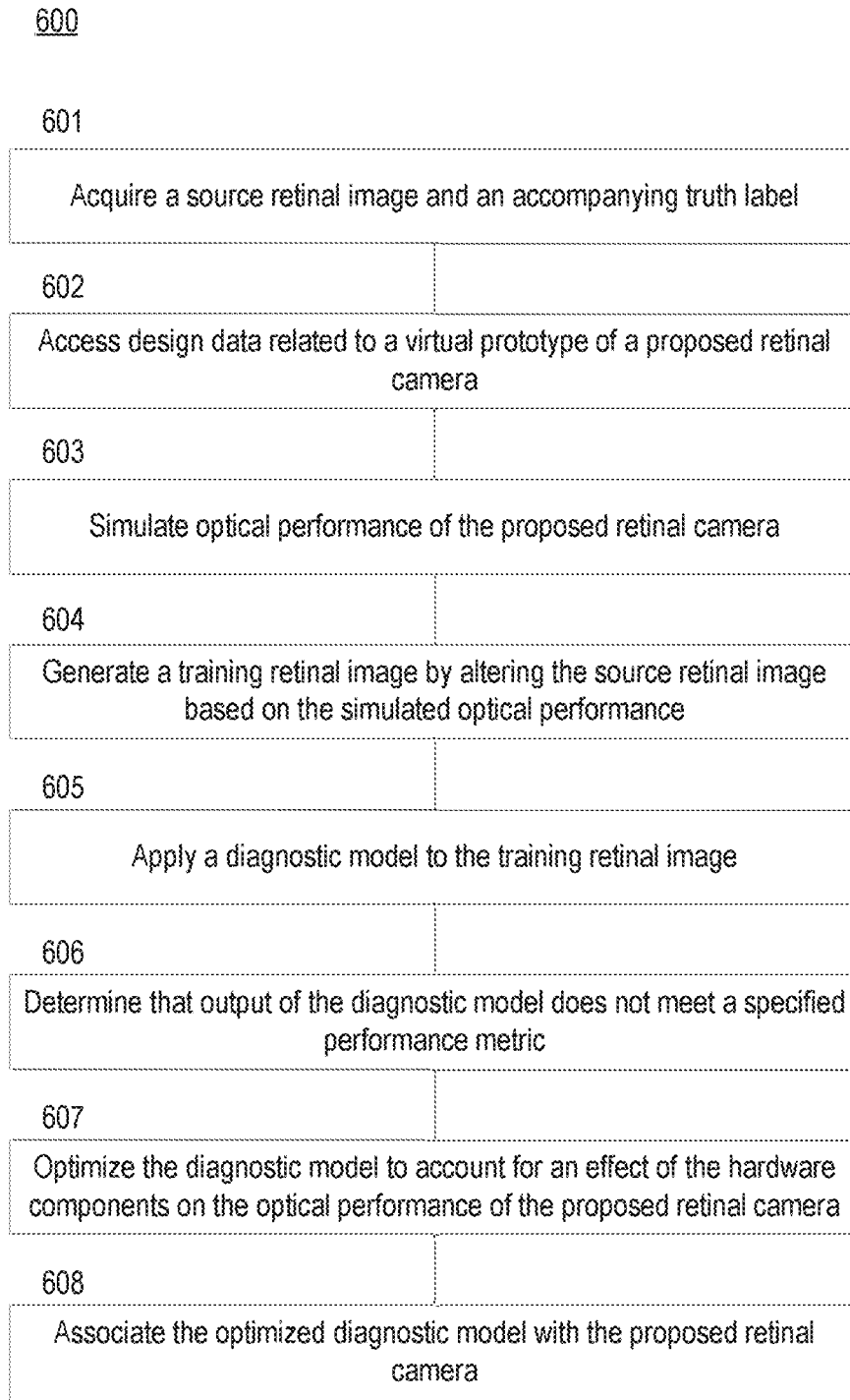
FIG. 6 depicts a flow diagram of a process for validating a diagnostic model associated with an ocular condition for a proposed retinal camera.

FIG. 6 depicts a flow diagram of a process 600 for validating a diagnostic model associated with an ocular condition for a proposed retinal camera. Because the diagnostic model can be validated based on design data associated with the proposed retinal camera, validation (and optimization, if necessary) can be performed because the proposed retinal camera is actually manufactured, deployed, etc.

Initially, a diagnostic platform can acquire a source retinal image and an accompanying truth label (step 601). The accompanying truth label may include a confirmed diagnosis of an ocular condition affecting an eye included in the source retinal image that was provided by a human grader. The term "confirmed diagnosis" can include affirmative diagnoses (e.g., an indication that the ocular condition is present) and negative diagnoses (e.g., an indication that the ocular condition is not present). Moreover, while some diagnostic models are binary classification models, other diagnostic models are multi-label classification modules. Thus, confirmed diagnoses need not necessarily be binary in nature. For example, if a diagnostic model to be optimized is associated with DR, then a confirmed diagnosis may specify whether the eye included in the source retinal image is healthy or suffering from mild, moderate, severe, or proliferate DR.

The human grader could be a researcher or a medical professional, such as an optometrist, ophthalmologist, etc. The source retinal image, meanwhile, may have been generated by a retinal camera that has already been validated by the Food and Drug Administration (FDA). That is, the source retinal image may have been generated by a retinal camera that has been approved for use by the FDA.

The diagnostic platform can then access design data related to a virtual prototype of a proposed retinal camera (step 602). The design data may specify characteristic(s) of a set of hardware components included in the proposed retinal camera with which visible light, non-visible light, or other electromagnetic waves in other frequency spectrums will interact when retinal images are generated. Electromagnetic waves may penetrate some hardware components (e.g., lenses) but reflect off others (e.g., mirrors). Thus, a hardware component may transmit, reflect, and/or transform electromagnetic waves in some manner. The diagnostic platform can then simulate optical performance of the proposed retinal camera by simulating how light rays will travel through its hardware components (step 603). That is, the diagnostic platform can simulate how light rays will travel along the optical path during the imaging process. By directly accessing the design data, the diagnostic platform can refrain from making assumptions about the proposed retinal camera. Instead, the diagnostic platform can more efficiently optimize diagnostic models by doing so while the proposed retinal camera is being designed.

The diagnostic platform can then generate a training retinal image by altering the source retinal image based on the simulated optical performance (step 604). For example, the diagnostic platform can augment the source retinal image by altering its pixel data. The training retinal image is intended to mimic the source retinal image as if generated by the proposed retinal camera. To generate the training retinal image, the diagnostic platform may augment the source retinal image by changing/introducing blurriness, resolution, contrast, white balance, shading, scattering, distortion, color aberrations, sharpening, compression, or any combination thereof. These augmentations may be in place of, or instead of, more conventional alterations such as rotating, mirroring, or altering an image property (e.g., hue or saturation).

The diagnostic platform can apply a diagnosis model associated with the ocular condition to the training retinal image (step 605), and then determine whether the output produced by the diagnostic model meets a specified performance metric. For example, if the diagnostic platform produced a single training retinal image, the diagnostic platform may determine whether the output (e.g., a proposed diagnosis of moderate DR) is substantially identical to the truth label that accompanied the source retinal image. As another example, if the diagnostic platform produced a series of training retinal images based on different source retinal images, the diagnostic platform may determine whether the application of the diagnostic model to the series of training retinal images results in an F1 score of greater than 0.85, 0.9, 0.95, etc.

In some instances, the diagnostic model will initially meet the specified performance metric. In such instances, the diagnostic platform can indicate that the diagnostic model has been verified for the proposed retinal camera and take no further action. However, in some instances, the diagnostic platform will determine that the output of the diagnostic model does not meet the specified performance metric (step 606). In such instances, the diagnostic platform can optimize the diagnostic model to account for effect(s) of the hardware components on the optical performance of the proposed retinal camera (step 607). For example, as further described above, the diagnostic platform may alter at least one of the algorithms that comprise the diagnostic model to account for the properties (e.g., resolution, hue, saturation, brightness, contrast) of images that will be generated by the proposed retinal camera.

Thereafter, the diagnostic platform can save the optimized diagnostic model to a database, and then associate the optimized diagnostic model with the proposed retinal camera (step 608). For example, the diagnostic platform may programmatically link the optimized diagnostic model to the proposed retinal camera to ensure that when a retinal image is received from the proposed retinal camera in the future, the optimized diagnostic model is applied rather than other diagnostic models associated with the same optical condition.

Figure 7:
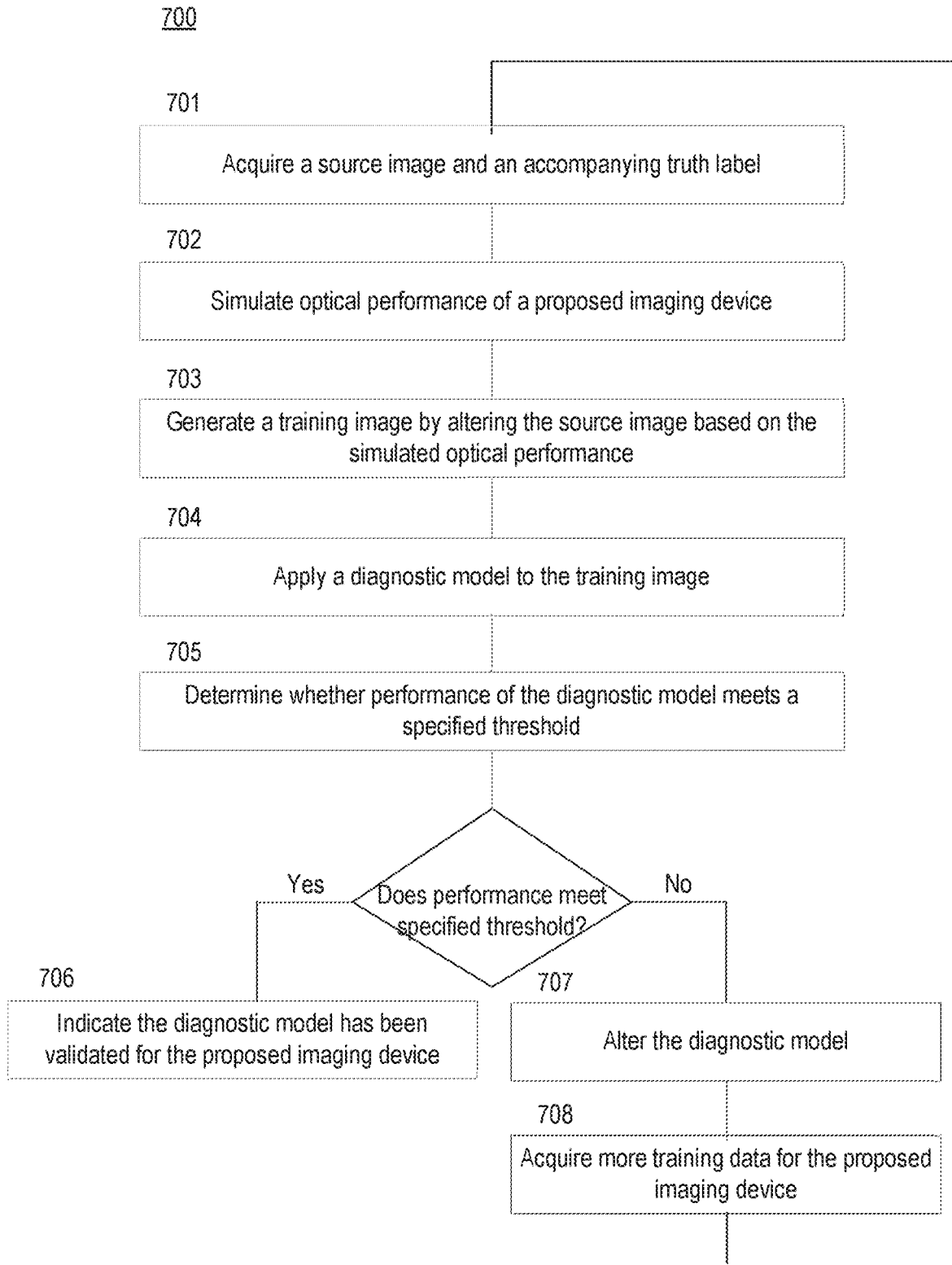
FIG. 7 depicts a flow diagram of a process for optimizing a diagnostic model associated with a medical condition for a proposed imaging device based on simulation.

FIG. 7 depicts a flow diagram of a process 700 for validating a diagnostic model associated with a medical condition for a proposed imaging device. Steps 701-705 of FIG. 7 are substantially similar to steps 601 and 603-606 of FIG. 6. Here, however, the diagnostic platform has simulated the optical performance of a proposed imaging device other than a retinal camera. Examples of imaging devices include, x-ray generators and detectors, MRI machines, CT machines, digital cameras (e.g., DSLR cameras and mirrorless cameras), etc. The technology described herein may also be applicable to microscopy imaging, ultrasound, positron-emission tomography (PET) imaging, elastography, photoacoustic imaging, laser speckle imaging, etc.

The diagnostic model is normally trained based on a large set of training images (e.g., on the order of millions of images). Then, the diagnostic model can be applied to a validation set of image(s) to determine whether the performance of the diagnostic model meets a specified threshold (step 705). The image(s) included in the validation set are generally not included in the set of training images. Moreover, the image(s) included in the validation set will generally satisfy a certain disease distribution. This allows the diagnostic platform to ensure that performance of the diagnostic model is appropriately studied across the entire spectrum of disease severities.

As described above, the diagnostic platform may determine whether the output is satisfactory on an individual basis (e.g., by determining whether the output substantially identical to the truth label that accompanied the source image) or a group basis (e.g., by determining whether a series of outputs are statistically similar to the truth labels that accompanies the source images). For example, the diagnostic platform may determine whether, for a given disease or a given imaging device, the output(s) (e.g., proposed diagnoses) produced by a diagnostic model are at least equivalent to the performance of medical professionals. Additionally or alternatively, the diagnostic platform may determine whether the output is satisfactory by examining input provided by an individual. For instance, an individual (e.g., an administrator or a medical professional) may specify whether the output produced by the diagnostic model for the training image has visually distinguished (e.g., via highlighting, outlining, etc.) the appropriate segment(s) (e.g., those determined to be diagnostically relevant).

If the performance of the diagnostic model meets the specified threshold, the diagnostic platform can indicate the diagnostic model has been validated for the proposed imaging device (step 706). However, if the performance of the diagnostic model does not meet the specified threshold, the diagnostic platform can alter the diagnostic model (step 707), and then acquire more training data for the proposed imaging device (step 708). More specifically, the diagnostic platform may acquire another source image and accompanying truth label, generate another training image by altering the other source image, apply the diagnostic model to the other training image, etc. In some embodiments, the diagnostic platform may reuse the original source image and accompanying truth label rather than acquire a new source image and accompanying truth label. Thus, the diagnostic platform may perform the process 700 multiple times in succession until the performance of the diagnostic model meets the specified threshold. For example, the diagnostic platform may continue performing the process 700, altering the diagnostic model each time the specified threshold is not met, until a specified number of consecutive applications of the diagnostic model (e.g., 10, 25, 100) meet the specified threshold.

The diagnostic platform can perform these steps automatically without requiring user input. Accordingly, the diagnostic platform may dynamically train the diagnostic model for a proposed imaging device upon receiving input that specifies design data for the proposed imaging device. Often, the diagnostic platform will produce a series of optimized diagnostic models corresponding to different medical conditions upon receiving input that specifies design data for the proposed imaging device. Such action can be performed in such a manner to ensure that, upon manufacture of the proposed imaging device, all diagnostic models that could be applied to images produced by the proposed imaging device have been optimized for the proposed imaging device.

FIG. 8 depicts a flow diagram of a process 800 for validating a diagnostic model associated with a medical condition. However, rather than alter a source image based on the simulated optical performance of a proposed imaging device, the diagnostic platform can instead perform image-to-image translation to discover the mapping between a source image (also referred to as an "input image") and a training image (also referred to as an "output image") using aligned image pair(s).

Initially, the diagnostic platform can acquire a first set of images generated by a first imaging device (step 801). The first set of images can include, for example, a series of retinal images associated with different subjects. The diagnostic platform can then identify a second imaging device for which a diagnostic model is to be optimized (step 802). In some embodiments the second imaging device is a virtual prototype of a proposed imaging device, while in other embodiments the second imaging device is a physical prototype of a proposed imaging device.

The diagnostic platform can then collect a second set of images generated by the second imaging device (step 803). Generally, the second set of images corresponds to the first set of images. For example, if the first set of images includes a series of retinal images associated with different subjects, then the second set of images includes another series of retinal images associated with the same subjects. Accordingly, the first and second sets of images may include images of the same subjects taken by different imaging devices.

Thereafter, the diagnostic platform can apply a translation algorithm to the first and second sets of images to discover how to translate a first image in the first set of images into a corresponding second image in the second set of images (step 804). The first and second images are generally associated with the same subject. The translation algorithm can determine what operation(s) are necessary to make the first and second images appear substantially identical to one another. Taken together, these operation(s) can be referred to as a "translation scheme." The translation scheme is indicative of a special augmentation needed to translate an image from a source domain to a target domain. An example of image-to-image translation is provided by Zhu et al. in "Unpaired Image-to-Image Translation using Cycle-Consistent Adversarial Networks," *International Conference on Computer Vision (ICCV)*, 2017.

The diagnostic platform can then optimize a diagnostic model for the second imaging device based on the translation scheme (step 805). As further described above, to optimize the diagnostic model, the diagnostic platform may alter the underlying algorithm(s). The diagnostic model may be related to the content of the first and second sets of images. For example, if the first and second sets of images include retinal images of subjects, the diagnostic platform may identify a diagnostic model for an optical condition that has been verified for the first imaging device and then alter the diagnostic model to personalize it for the second imaging device.

The optimized diagnostic model can then be saved in a database (step 806) and associated with the second imaging device (step 807). For example, the diagnostic platform may programmatically link the optimized diagnostic model to the second imaging device to ensure that when a retinal image is received from the second imaging device in the future, the optimized diagnostic model is applied rather than the original diagnostic model (and any other diagnostic models optimized for other imaging devices).

Unless contrary to physical possibility, it is envisioned that the steps described above may be performed in various sequences and combinations. For example, the diagnostic platform may be configured to optimize a diagnostic model for an imaging device by performing the process 700 of FIG. 7 and the process 800 of FIG. 8. In such embodiments, the diagnostic model may be trained using two sets of images (e.g., a first set created by simulating optical performance of the imaging device, and a second set created by the imaging device).

Other steps may also be included in some embodiments. For example, the diagnostic platform may be able to receive input specifying a requested alteration of the diagnostic model. That is, the diagnostic platform may be able to receive instructions manually input by an individual (e.g., an administrator responsible for developing/training diagnostic models) regarding how to alter the diagnostic model. These instructions may be provided instead of, or in addition to, the optimization automatically performed by the diagnostic platform.

As another example, the diagnostic platform may be able to receive input specifying a requested alteration of a proposed imaging device. For instance, after observing the performance of the diagnostic model, an individual may choose to alter the virtual prototype of the proposed imaging device (e.g., by adding, removing, or altering a mechanical component such as a lens). The diagnostic platform may be configured to automatically complete the optimization process once again responsive to determining that the virtual prototype has been altered. Such a feature enables the individual to quickly observe the effect of different optical/mechanical designs in a short period of time.

Processing System

Figure 9:
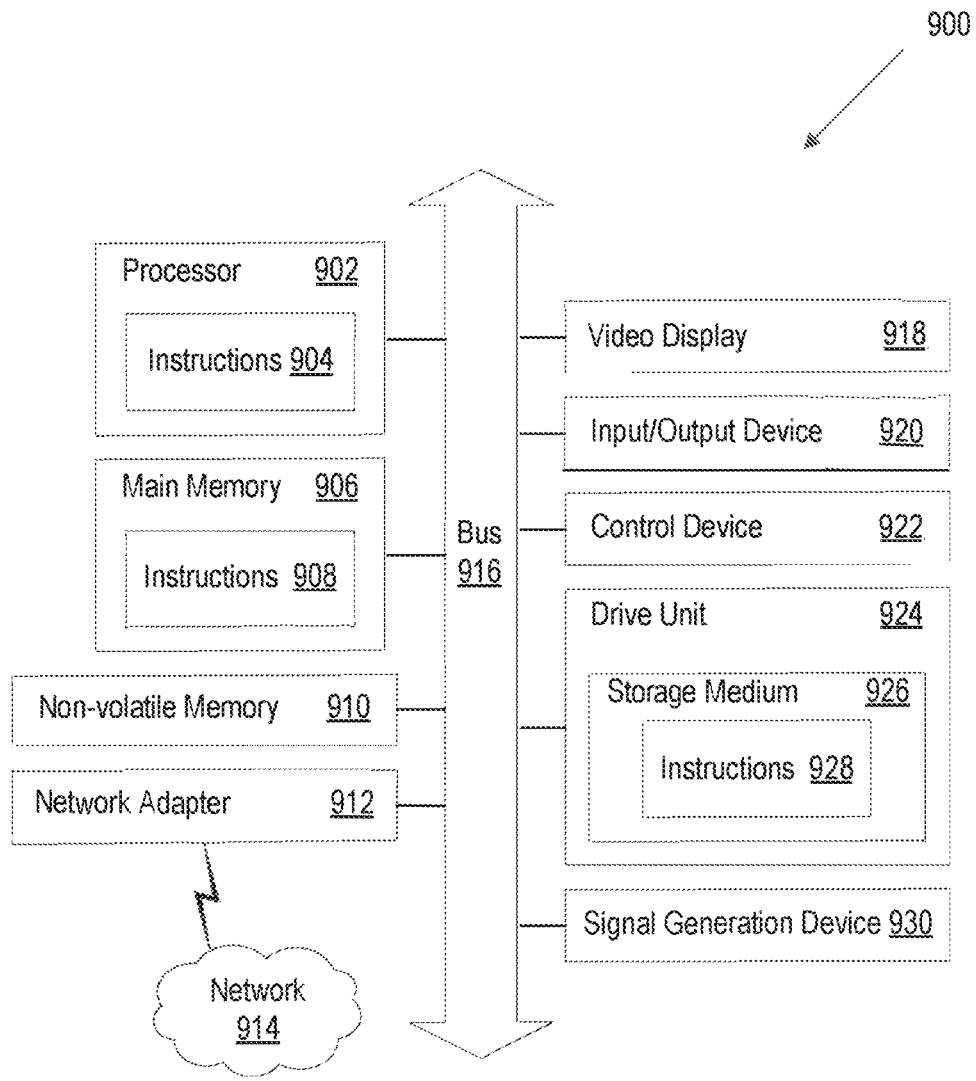
FIG. 9 is a block diagram illustrating an example of a processing system in which at least some operations described herein can be implemented.

FIG. 9 is a block diagram illustrating an example of a processing system 900 in which at least some operations described herein can be implemented. For example, some components of the processing system 900 may be hosted on a computing device that includes a diagnostic platform (e.g., diagnostic platform 302 of FIG. 3).

The processing system 900 may include one or more central processing units ("processors") 902, main memory 906, non-volatile memory 910, network adapter 912 (e.g., network interface), video display 918, input/output devices 920, control device 922 (e.g., keyboard and pointing devices), drive unit 924 including a storage medium 926, and signal generation device 930 that are communicatively connected to a bus 916. The bus 916 is illustrated as an abstraction that represents one or more physical buses and/or point-to-point connections that are connected by appropriate bridges, adapters, or controllers. The bus 916, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 900 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 900.

While the main memory 906, non-volatile memory 910, and storage medium 926 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 928. The term "machine-readable medium" and "storage medium" shall also be taken to include any medium that is capable of storing, encoding, or carrying a set of instructions for execution by the processing system 900.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 904, 908, 928) set at various times in various memory and storage devices in a computing device. When read and executed by the one or more processors 902, the instruction(s) cause the processing system 900 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 910, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 912 enables the processing system 900 to mediate data in a network 914 with an entity that is external to the processing system 900 through any communication protocol supported by the processing system 900 and the external entity. The network adapter 912 can include a network adaptor card, a wireless network interface card, a router, an access point, a wireless router, a switch, a multi-layer switch, a protocol converter, a gateway, a bridge, bridge router, a hub, a digital media receiver, and/or a repeater.

The network adapter 912 may include a firewall that governs and/or manages permission to access/proxy data in a computer network, as well as tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A computer-implemented method comprising:
acquiring a source retinal image and an accompanying truth label,
wherein the accompanying truth label represents a confirmed diagnosis of an ocular condition affecting an eye included in the source retinal image;
accessing design data related to a virtual prototype of a retinal camera that includes a set of hardware components with which electromagnetic waves will interact when retinal images are generated by the retinal camera;
predicting optical performance of the retinal camera by simulating an interaction of electromagnetic waves with the set of hardware components; and
producing, based on the predicted optical performance, a training retinal image by altering pixel data of the source retinal image,
wherein the training retinal image is intended to represent the source retinal image as if generated by the retinal camera, and
wherein the training retinal image is associated with the accompanying truth label corresponding to the source retinal image and formatted for use to train a diagnostic model associated with the ocular condition.

2. The method of claim 1, further comprising:
training the diagnostic model with the training retinal image and the accompanying truth label corresponding to the source retinal image;
applying the diagnostic model to the training retinal image to produce a proposed diagnosis;
comparing the proposed diagnosis to the accompanying truth label; and
in response to a determination that the proposed diagnosis differs from the accompanying truth label, altering the diagnostic model to optimize the diagnostic model for the retinal camera.

3. The method of claim 2, wherein said applying comprises:
applying multiple algorithms to the altered pixel data corresponding to the training retinal image.

4. The method of claim 3, further comprising:
altering the diagnostic model by modifying at least one algorithm of the multiple algorithms in such a manner to ensure that a subsequent application of the altered diagnostic model to the training retinal image will produce a subsequent proposed diagnosis that is substantially identical to the accompanying truth label.

5. The method of claim 4, further comprising:
storing the altered diagnostic model in a memory; and
associating the altered diagnostic model with the retinal camera in a database record.

6. The method of claim 5, wherein said associating programmatically links the altered diagnostic model to the retinal camera to ensure that the altered diagnostic model is applied to retinal images generated by the retinal camera in the future.

7. The method of claim 1, further comprising:
retrieving the diagnostic model from a library of diagnostic models, wherein each diagnostic model in the library of diagnostic models corresponds to a different ocular condition; and training the diagnostic model with the training retinal image and the accompanying truth label corresponding to the source retinal image.

8. The method of claim 1, wherein said predicting comprises:

transmitting the design data related to the virtual prototype of the retinal camera to a computer program,
wherein the computer program is designed to simulate the interaction of electromagnetic waves with the set of hardware components; and
receiving, from the computer program, output indicative of the predicted optical performance.

9. The method of claim 1, wherein pixel data of the source retinal image is altered by changing blurriness, contrast, white balance, shading, scattering, distortion, color aberration, sharpening, compression, or any combination thereof.

10. A method comprising:

acquiring, by a processor, a source image and an accompanying truth label,
wherein the accompanying truth label represents a confirmed diagnosis of a medical condition affecting a human body part included in the source image;
simulating, by the processor, an electromagnetic transformation function of a proposed imaging device by—
accessing design data related to a virtual prototype of the proposed imaging device, and
predicting, based on the design data, the transmission of light through the proposed imaging device during an imaging operation, so as to establish optical performance of the proposed imaging device;
altering, by the processor based on said simulating, the source image to produce a training image that is representative of the source image as if generated by the proposed imaging device; and
training, by the processor, a diagnostic model associated with the medical condition with the training image and the accompanying truth label corresponding to the source image.

11. The method of claim 10, wherein said training comprises:

applying the diagnostic model to the training image,
determining that an output produced by the diagnostic model does not meet a specified performance metric, and
optimizing the diagnostic model for the proposed imaging device.

12. The method of claim 11, wherein said optimizing comprises:

modifying at least one algorithm applied as part of the diagnostic model in such a manner to ensure that a subsequent application of the diagnostic model to the training image will produce an output that meets the specified performance metric.

13. The method of claim 11, wherein the output produced by the diagnostic model is a proposed diagnosis regarding the medical condition as determined based on an analysis of pixel data corresponding to the training image.

14. The method of claim 13, wherein said determining comprises:

examining whether the proposed diagnosis is substantially identical to the accompanying truth label.

15. The method of claim 13, wherein the diagnosis model is a classification model that employs one or more statistical techniques to pixel data corresponding to the training image to produce the proposed diagnosis.

16. The method of claim 11, wherein said determining comprises:

examining input provided by an individual that specifies whether the output meets the specified performance metric.

17. The method of claim 10, further comprising:

parsing, by the processor, the design data to identify a set of hardware components through which the light will extend during the imaging operation.

18. The method of claim 10, wherein said altering comprises:

changing blurriness, contrast, white balance, shading, scattering, distortion, color aberration, sharpening, compression, or any combination thereof.

19. A non-transitory medium with instructions stored thereon that, when executed by a processor of an electronic device, cause the electronic device to perform operations comprising:

acquiring (i) a first image and (ii) an accompanying truth label that is representative of a confirmed diagnosis of a medical condition affecting a human body part included in the first image;
predicting optical performance of an imaging device by—
accessing design data that is associated with the imaging device, and
simulating the transmission of light through the imaging device during an imaging operation using the design data; and
generating a second image by modifying the first image based on the predicted optical performance,
wherein the second image is modified so as to represent the first image as if generated by the imaging device.

20. The non-transitory medium of claim 19, wherein the operations further comprise:

training a diagnostic model associated with the medical condition with (i) the second image and (ii) the accompanying truth label corresponding to the first image.

21. The non-transitory medium of claim 20, wherein the operations further comprise:

applying a diagnostic model associated with the medical condition to the second image, so as to produce an output; and
determining whether performance of the diagnostic model meets a threshold based on an analysis of the output.

22. The non-transitory medium of claim 21, wherein the operations further comprise:

in response to a determination that the performance meets the threshold,
indicating that the diagnostic model has been validated in a data structure that is associated with the imaging device.

23. The non-transitory medium of claim 21, wherein the operations further comprise:

in response to a determination that the performance does not meet the threshold, altering the diagnostic model,
obtaining a third image that is modified as if generated by the imaging device, and
training the diagnostic model associated with the medical condition with the third image.

24. The non-transitory medium of claim 23, wherein said obtaining comprises:

acquiring (i) a fourth image and (ii) another accompanying truth label that is representative of another confirmed diagnosis of the medical condition affecting another human body part included in the fourth image, wherein the fourth image is associated with a different person than the first image, and generating the third image by modifying the fourth image based on the predicted optical performance.

25. The non-transitory medium of claim 21, wherein the second image is one of multiple images to which the diagnostic model is applied to determine whether the performance meets the threshold, and wherein the multiple images satisfy a disease distribution with respect to the medical condition, such that an entire spectrum of disease severities of the medical condition is covered by the multiple images.

\* \* \* \* \*